United States Patent
Fukuda

(10) Patent No.: US 12,133,756 B2
(45) Date of Patent: Nov. 5, 2024

(54) IMAGE PROCESSING DEVICE, RADIOGRAPHY SYSTEM, IMAGE PROCESSING METHOD, AND IMAGE PROCESSING PROGRAM

(71) Applicant: FUJIFILM CORPORATION, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 394 days.

(21) Appl. No.: 17/694,695

(22) Filed: Mar. 15, 2022

(65) Prior Publication Data

US 2022/0304644 A1    Sep. 29, 2022

(30) Foreign Application Priority Data

Mar. 24, 2021 (JP) .................................. 2021-050392

(51) Int. Cl.
| | |
|---|---|
| *A61B 6/00* | (2024.01) |
| *A61B 6/02* | (2006.01) |
| *G06T 7/00* | (2017.01) |

(52) U.S. Cl.
CPC ............ *A61B 6/5205* (2013.01); *A61B 6/025* (2013.01); *G06T 7/0012* (2013.01); *G06T 2207/10112* (2013.01); *G06T 2207/30068* (2013.01)

(58) Field of Classification Search
CPC ....... A61B 6/5205; A61B 6/025; A61B 6/502; A61B 6/032; A61B 6/0492; A61B 6/584;
(Continued)

(56) References Cited

U.S. PATENT DOCUMENTS

| | | | |
|---|---|---|---|
| 11,596,369 B2 * | 3/2023 | Hong ..................... | A61B 6/547 |
| 2002/0131559 A1 | 9/2002 | Launay et al. | |

(Continued)

FOREIGN PATENT DOCUMENTS

| | | |
|---|---|---|
| JP | 2003-24321 A | 1/2003 |
| JP | 2008-110098 A | 5/2008 |

(Continued)

OTHER PUBLICATIONS

English language translation of the following: Notice dated Jul. 30, 2024 from the JPO in a Japanese patent application No. 2021-050392 corresponding to the instant patent application. This office action translation is submitted now in order to supplement the understanding of the cited references which are being disclosed in the instant Information Disclosure Statement.

*Primary Examiner* — Jose L Couso
(74) *Attorney, Agent, or Firm* — SOLARIS Intellectual Property Group, PLLC

(57) ABSTRACT

A CPU acquires projection images captured at each irradiation position in a state in which a marker is disposed and set irradiation positions set as the irradiation positions of the projection images, generates a tomographic image from the projection images using the set irradiation positions, derives the coordinates of a three-dimensional position where the marker is disposed from the tomographic image, derives a first two-dimensional position of the marker projected onto the projection plane from the set irradiation positions and the coordinates of the three-dimensional position of the marker, and estimates the irradiation positions on the basis of the first two-dimensional position and a second two-dimensional position of the marker in the projection plane which is specified from a marker image indicating the marker included in each of the projection images.

14 Claims, 10 Drawing Sheets

(58) Field of Classification Search
CPC ....... A61B 6/587; A61B 6/588; G06T 7/0012; G06T 2207/10112; G06T 2207/30068; G06T 11/005; G06T 2207/10081; G06T 7/70; G06T 7/246; G06T 2207/10016; G06T 2207/10116; G06T 2207/30004; G06T 2207/30204; G06T 2207/30241
See application file for complete search history.

(56) References Cited

U.S. PATENT DOCUMENTS

| | | | |
|---|---|---|---|
| 2005/0113682 A1* | 5/2005 | Webber | A61B 6/05 378/4 |
| 2007/0189436 A1* | 8/2007 | Goto | A61B 6/4085 382/131 |
| 2008/0101536 A1 | 5/2008 | Sendai | |
| 2012/0014498 A1 | 1/2012 | Akahori | |
| 2014/0119500 A1 | 5/2014 | Akahori | |
| 2015/0265186 A1 | 9/2015 | Kuwabara | |
| 2016/0063740 A1* | 3/2016 | Sakimoto | G06T 11/005 378/20 |
| 2017/0231589 A1* | 8/2017 | Fujii | A61B 6/032 |
| 2019/0069834 A1 | 3/2019 | Morita | |
| 2021/0183062 A1 | 6/2021 | Fukuda | |
| 2021/0393225 A1 | 12/2021 | Morita | |

FOREIGN PATENT DOCUMENTS

| | | | | |
|---|---|---|---|---|
| JP | 2012-20023 A | 2/2012 | | |
| JP | 2013-13651 A | 1/2013 | | |
| JP | 2015-177884 A | 10/2015 | | |
| JP | 2015-188604 A | 11/2015 | | |
| JP | 2019-47837 A | 3/2019 | | |
| KR | 101523422 B1 * | 5/2015 | ............ | A61B 6/025 |
| KR | 101819257 B1 * | 1/2018 | ............ | A61B 6/466 |
| WO | WO-2013157457 A1 * | 10/2013 | ............ | A61B 6/12 |
| WO | 2020/059306 A1 | 3/2020 | | |
| WO | 2020/194844 A1 | 10/2020 | | |

* cited by examiner

IMAGE PROCESSING DEVICE, RADIOGRAPHY SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-050392 filed on Mar. 24, 2021. The above application is hereby expressly incorporated by reference, in its entirety, into the present application.

BACKGROUND OF THE INVENTION

1. Technical Field

The present disclosure relates to an image processing device, a radiography system, an image processing method, and an image processing program.

2. Description of the Related Art

In general, so-called tomosynthesis imaging is known which irradiates an object with radiation emitted from a radiation source at each of a plurality of irradiation positions having different irradiation angles to capture a plurality of projection images of the object at different irradiation positions.

A technique is known which generates a tomographic image from a projection image using a radiation source position of a radiation source in a case in which the projection image is captured. For example, a reconstruction processing method, such as a filter back projection (FBP) method or an iterative reconstruction method, which is known as a tomographic image generation method generates a tomographic image on the basis of the radiation source position of the radiation source in a three-dimensional space and the two-dimensional position of each pixel of the projection image. Therefore, in a case in which the radiation source position of the radiation source is inaccurate, the accuracy of the tomographic image generated using the inaccurate radiation source position may be reduced.

Therefore, a technique is known which acquires an accurate radiation source position of a radiation source. For example, JP2013-13651A discloses a technique which calibrates the position of a radiation source on the basis of a relative relationship between the positions of marker images included in a plurality of projection images obtained by imaging a marker.

SUMMARY

In the technique according to the related art, in a case in which the irradiation position where the radiation source is located is derived using the projection image obtained by imaging the marker, the accuracy of deriving the irradiation position may be reduced.

The present disclosure has been made in view of the above circumstances, and an object of the present disclosure is to provide an image processing device, a radiography system, an image processing method, and an image processing program that can derive an irradiation position of radiation with high accuracy.

In order to achieve the above object, according to a first aspect of the present disclosure, there is provided an image processing device that processes a plurality of projection images obtained by irradiating an object with radiation emitted from a radiation source at each of a plurality of irradiation positions having different irradiation angles. The image processing device comprises at least one processor. The processor acquires a plurality of projection images captured at each of the irradiation positions in a state in which a marker is disposed between the plurality of irradiation positions and a projection plane, and a plurality of set irradiation positions set as the irradiation positions of the plurality of projection images, generates a first tomographic image from the plurality of projection images using the plurality of set irradiation positions, derives a first three-dimensional position where the marker is disposed from the first tomographic image, derives a first projection plane position of the marker projected onto the projection plane from the plurality of set irradiation positions and the first three-dimensional position of the marker, and estimates the plurality of irradiation positions on the basis of the first projection plane position and a second projection plane position of the marker in the projection plane which is specified from a marker image indicating the marker included in each of the plurality of projection images.

According to a second aspect of the present disclosure, in the image processing device according to the first aspect, the processor may estimate the plurality of irradiation positions where the plurality of first projection plane positions and the second projection plane positions are matched with each other.

According to a third aspect of the present disclosure, in the image processing device according to the first aspect or the second aspect, the processor may further estimate a second three-dimensional position of the marker on the basis of the plurality of first projection plane positions and the second projection plane positions.

According to a fourth aspect of the present disclosure, in the image processing device according to any one of the first to third aspects, the processor may generate a second tomographic image from the plurality of projection images using the estimated plurality of irradiation positions.

According to a fifth aspect of the present disclosure, in the image processing device according to the third aspect, the processor may generate a second tomographic image up to a height corresponding to the second three-dimensional position in a height direction from the plurality of projection images, using the estimated plurality of irradiation positions.

According to a sixth aspect of the present disclosure, in the image processing device according to the third aspect or the fifth aspect, the processor may acquire the plurality of projection images of a breast which is the object and is compressed by a compression member provided with the marker and estimate a thickness of the breast in a compressed state on the basis of the second three-dimensional position.

According to a seventh aspect of the present disclosure, in the image processing device according to the sixth aspect, the processor may derive information related to an amount of mammary glands of the breast on the basis of the thickness.

According to an eighth aspect of the present disclosure, in the image processing device according to the sixth aspect, the processor may estimate an amount of scattered radiation on the basis of the thickness.

According to a ninth aspect of the present disclosure, in the image processing device according to any one of the first to eighth aspects, a plurality of the markers may be disposed between the plurality of irradiation positions and the projection plane.

According to a tenth aspect of the present disclosure, in the image processing device according to any one of the first to ninth aspects, the processor may estimate the plurality of irradiation positions where the plurality of first projection plane positions and the second projection plane positions are matched with each other by repeatedly updating the plurality of set irradiation positions and the first three-dimensional position to repeatedly derive the first projection plane positions.

According to an eleventh aspect of the present disclosure, in the image processing device according to the tenth aspect, a plurality of the markers may be disposed according to a predetermined disposition condition, and the processor may update the first three-dimensional position within a range of the disposition condition.

In addition, in order to achieve the above object, according to a twelfth aspect of the present disclosure, there is provided a radiography system comprising: a radiation source that generates radiation; a radiography apparatus that performs tomosynthesis imaging which irradiates an object with the radiation emitted from the radiation source at each of a plurality of irradiation positions having different irradiation angles to capture projection images of the object at each of the irradiation positions; and the image processing device according to the present disclosure.

Further, in order to achieve the above object, according to a thirteenth aspect of the present disclosure, there is provided an image processing method that is executed by a computer and that processes a plurality of projection images obtained by irradiating an object with radiation emitted from a radiation source at each of a plurality of irradiation positions having different irradiation angles. The image processing method comprises: acquiring a plurality of projection images captured at each of the irradiation positions in a state in which a marker is disposed between the plurality of irradiation positions and a projection plane, and a plurality of set irradiation positions set as the irradiation positions of the plurality of projection images; generating a first tomographic image from the plurality of projection images using the plurality of set irradiation positions; deriving a first three-dimensional position where the marker is disposed from the first tomographic image; deriving a first projection plane position of the marker projected onto the projection plane from the plurality of set irradiation positions and the first three-dimensional position of the marker; and estimating the plurality of irradiation positions on the basis of the first projection plane position and a second projection plane position of the marker in the projection plane which is specified from a marker image indicating the marker included in each of the plurality of projection images.

Furthermore, in order to achieve the above object, according to a fourteenth aspect of the present disclosure, there is provided an image processing program that processes a plurality of projection images obtained by irradiating an object with radiation emitted from a radiation source at each of a plurality of irradiation positions having different irradiation angles. The image processing program causes a computer to perform a process comprising: acquiring a plurality of projection images captured at each of the irradiation positions in a state in which a marker is disposed between the plurality of irradiation positions and a projection plane, and a plurality of set irradiation positions set as the irradiation positions of the plurality of projection images; generating a first tomographic image from the plurality of projection images using the plurality of set irradiation positions; deriving a first three-dimensional position where the marker is disposed from the first tomographic image; deriving a first projection plane position of the marker projected onto the projection plane from the plurality of set irradiation positions and the first three-dimensional position of the marker; and estimating the plurality of irradiation positions on the basis of the first projection plane position and a second projection plane position of the marker in the projection plane which is specified from a marker image indicating the marker included in each of the plurality of projection images.

According to the present disclosure, it is possible to derive the irradiation position of radiation with high accuracy.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In addition, this embodiment does not limit the present disclosure.

Figure 1:
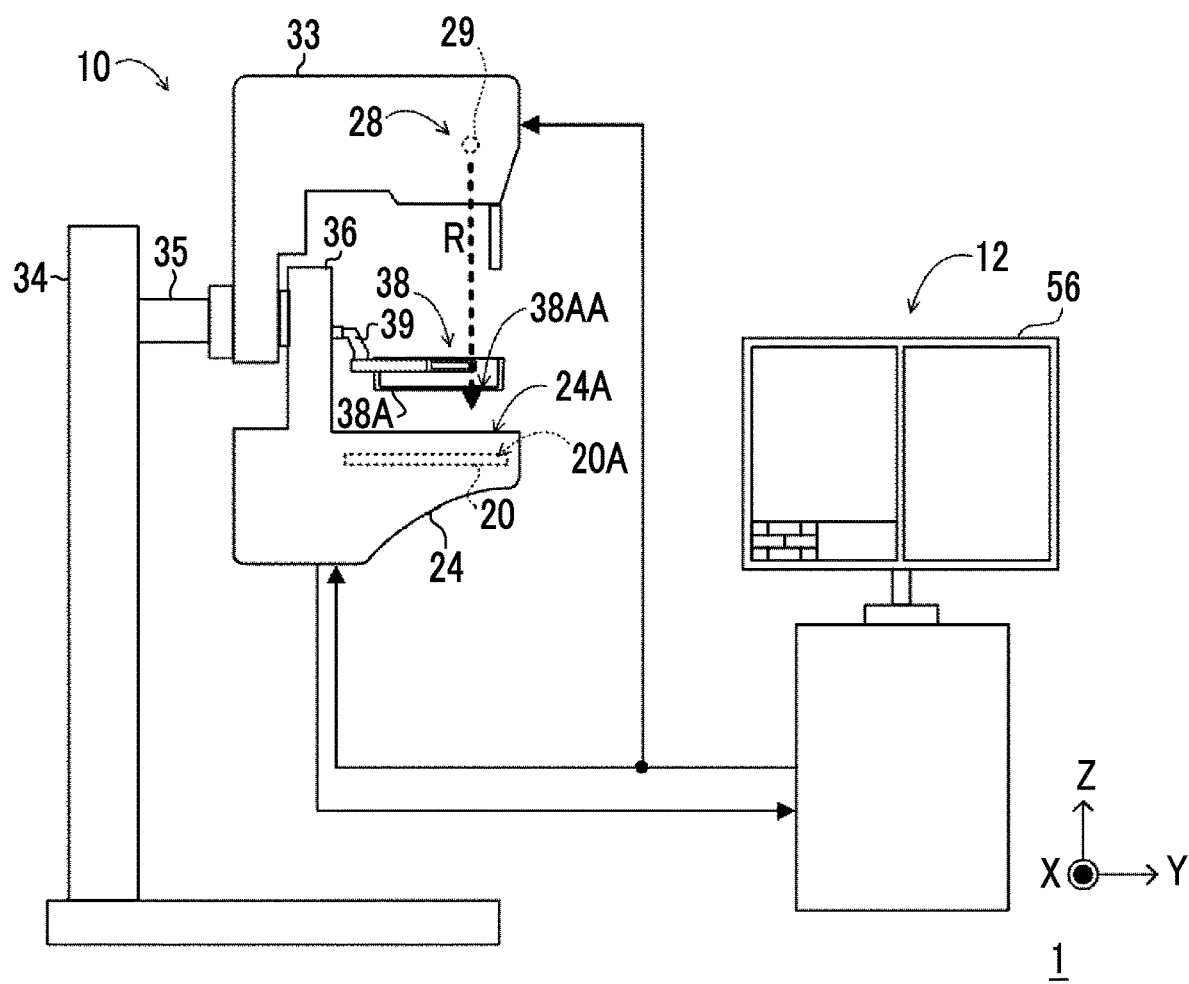
FIG. 1 is a diagram schematically illustrating an example of the overall configuration of a radiography system according to an embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from a left side of a subject.

The mammography apparatus 10 according to this embodiment is an apparatus that is operated under the control of the console 12 and that irradiates a breast of the subject as an object with radiation R (for example, X-rays) to capture a radiographic image of the breast. In addition, the mammography apparatus 10 may be an apparatus that images the breast of the subject not only in a state in which the subject is standing (standing state) but also in a state in which the subject is sitting on, for example, a chair (including a wheelchair) (sitting state).

Furthermore, the mammography apparatus 10 according to this embodiment has a function of performing normal imaging that captures images at an irradiation position where a radiation source 29 is disposed along a normal direction to a detection surface 20A of a radiation detector 20 and so-called tomosynthesis imaging that captures images while moving the radiation source 29 to each of a plurality of irradiation positions.

The radiation detector 20 detects the radiation R transmitted through the breast which is the object. Specifically, the radiation detector 20 detects the radiation R that has entered the breast of the subject and an imaging table 24 and that has reached the detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". A plurality of pixels corresponding to the radiographic image generated by the radiation detector 20 are disposed in a matrix on the detection surface 20A of the radiation detector 20 according to this embodiment. The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 that is used to compress the breast in a case in which imaging is performed is attached to a compression unit 36 that is provided in the imaging table 24. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24. The compression plate 38 according to this embodiment is an example of a compression member according to the present disclosure.

Figure 2:
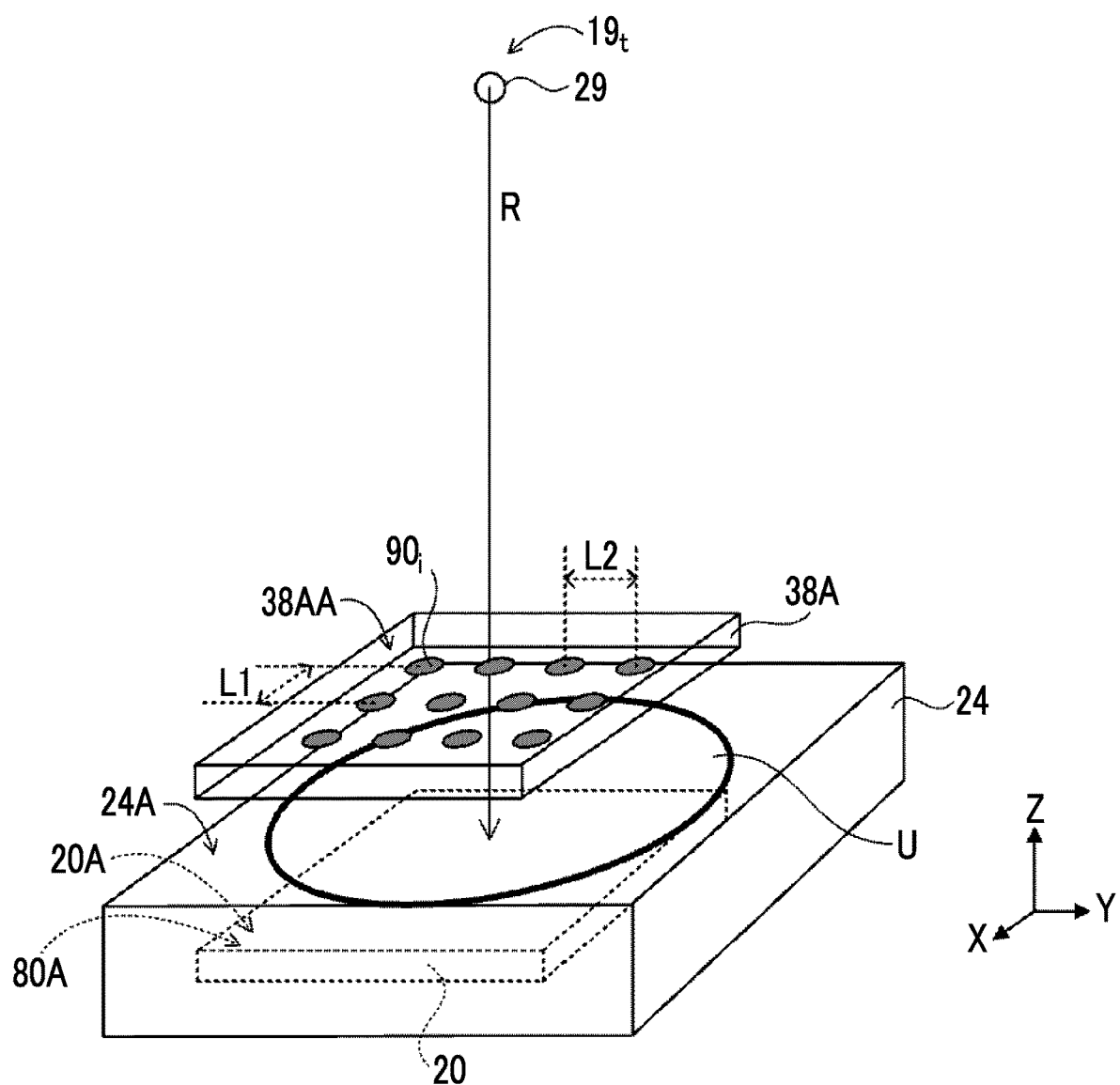
FIG. 2 is a diagram illustrating a plurality of markers provided on a compression plate.

As illustrated in FIGS. 1 and 2, the compression plate 38 according to this embodiment includes a compression portion 38A that comes into contact with the breast and compresses the breast. A plurality of markers $90_i$ (i=1, 2, ..., the maximum value is 12 in FIG. 3) are provided at an interval of L1 in the X direction and at an interval of L2 in the Y direction on an upper surface 38AA of the compression portion 38A that is opposite to a compression surface coming into contact with the breast. The markers $90_i$ are used to estimate irradiation positions $19_t$ in the tomosynthesis imaging. The estimation of the irradiation positions $19_t$ using the markers $90_i$ will be described in detail below. The markers $90_i$ are formed of a material that appears in a radiographic image. Therefore, a material that absorbs the radiation R is preferable as the material forming the markers $90_i$. Examples of the material that absorbs the radiation R include metal, such as lead, and ultraviolet (UV) cut glass made of a UV absorbing material. In addition, it is preferable that the compression portion 38A of the compression plate 38 is transparent in order for the user to easily check the shape and position of the breast in a compressed state in a case in which the breast is compressed and positioned by the compression plate 38. Therefore, it is preferable that the markers $90_i$ are also transparent and are made of a transparent material such as UV cut glass.

In addition, the position and number of markers $90_i$ provided are not limited to this embodiment. The position where the marker $90_i$ is provided may be any position between the irradiation position $19_t$ and the detection surface 20A of the radiation detector 20 which is a projection plane 80A of a projection image in a case in which the projection image is captured. Further, the number of markers $90_i$ provided may be set according to, for example, the accuracy of estimating the irradiation positions $19_t$ or the size of a region in which the markers $90_i$ are provided (the size of the upper surface 38AA in FIG. 2). In the following description, for example, for the coordinates of the position corresponding to each marker $90_i$, a reference letter "i" indicating the marker $90_i$ is added to the reference numeral indicating each image.

As illustrated in FIG. 1, the mammography apparatus 10 according to this embodiment comprises the imaging table 24, an arm portion 33, a base 34, and a shaft portion 35. The arm portion 33 is held by the base 34 to be movable in the up-down direction (Z-axis direction). In addition, the arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36 of the imaging table 24. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between transmission and non-transmission of power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this embodiment, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

Figure 3:
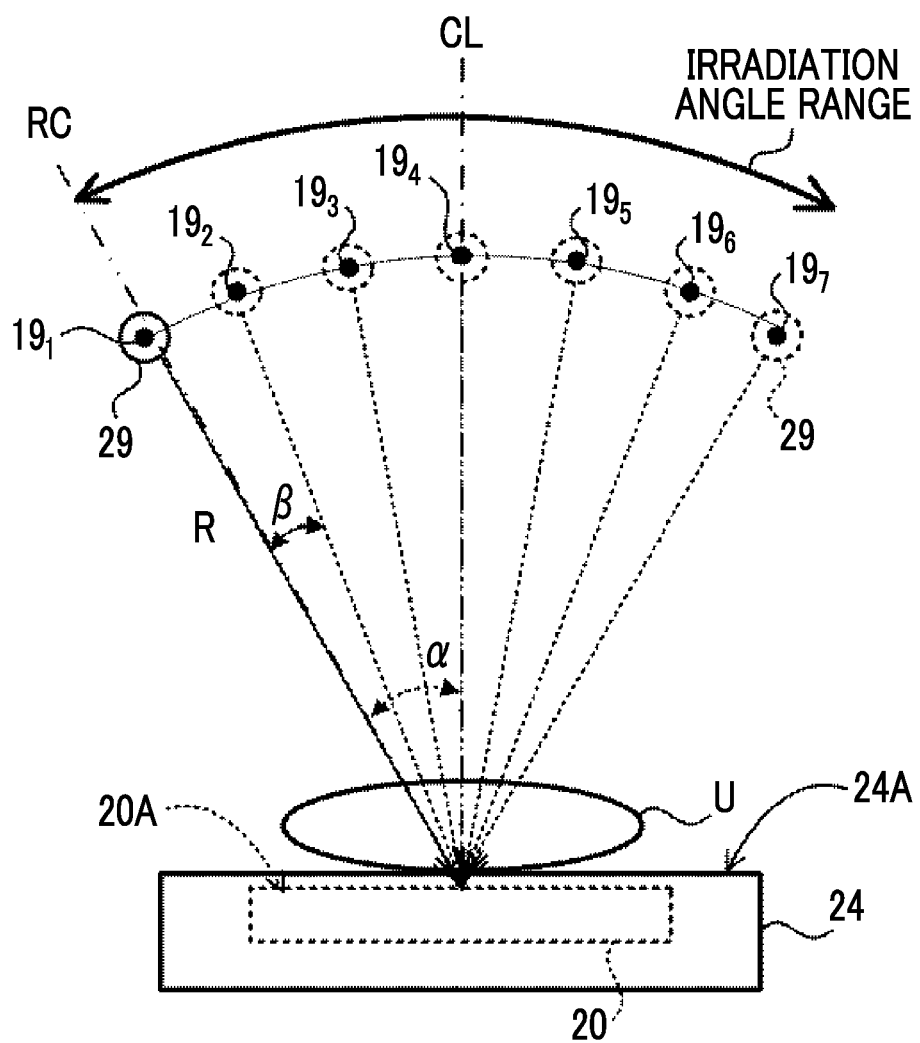
FIG. 3 is a diagram illustrating an example of tomosynthesis imaging.

In a case in which the mammography apparatus 10 performs the tomosynthesis imaging, the radiation source 29 of a radiation emitting unit 28 is sequentially moved to each of the plurality of irradiation positions having different irradiation angles by the rotation of the arm portion 33. The radiation source 29 includes a radiation tube (not illustrated) that generates the radiation R, and the radiation tube is moved to each of the plurality of irradiation positions according to the movement of the radiation source 29. FIG. 3 is a diagram illustrating an example of the tomosynthesis imaging. In addition, the compression plate 38 is not illustrated in FIG. 3. In this embodiment, as illustrated in FIG. 3, the radiation source 29 is moved to the irradiation positions $19_t$ (t=1, 2, . . . ; the maximum value is 7 in FIG. 3) having different irradiation angles which are disposed at an interval of a predetermined angle θ, that is, the positions where the irradiation angles of the radiation R with respect to the detection surface 20A of the radiation detector 20 are different. At each of the irradiation positions $19_r$, the radiation source 29 emits the radiation R to an object U in response to an instruction from the console 12, and the radiation detector 20 captures a radiographic image.

In the radiography system 1, in a case in which the tomosynthesis imaging that moves the radiation source 29 to each of the irradiation positions $19_t$ and that captures radiographic images at each of the irradiation positions $19_t$ is performed, seven radiographic images are obtained in the example illustrated in FIG. 3. In this embodiment, for example, as illustrated in FIG. 3, a case in which seven projection images are obtained at the irradiation positions $19_1$ to $19_7$ in the tomosynthesis imaging will be described. In addition, in this embodiment, in the tomosynthesis imaging, in a case in which a radiographic image captured at each irradiation position $19_t$ is distinguished from other radiographic images, it is referred to as a "projection image". Further, in a case in which a radiographic image is generically referred to regardless of the type, such as a projection image and a tomographic image which will be described below, it is simply referred to as a "radiographic image". Furthermore, in the following description, in a case in which the irradiation positions $19_t$ are generically referred to, a reference letter t for distinguishing each irradiation position is omitted, and the irradiation positions $19_t$ are referred to as "irradiation positions 19". Further, in the following description, for the image corresponding to the irradiation position $19_t$, such as the projection image captured at each irradiation position $19_t$, the reference letter t indicating the irradiation position $19_t$ is given to the reference numeral indicating each image.

Further, in this embodiment, set irradiation positions $19V_t$ are preset as each irradiation position which is used in a case in which a second tomographic image generation unit, which will be described in detail below, generates tomographic images 82 (see FIG. 8) in the tomosynthesis imaging. A design irradiation position is given as an example of the set irradiation position $19V_t$. However, the irradiation position $19_r$, which is the actual position of the radiation source 29 in a case in which the projection image 80 is captured in the tomosynthesis imaging, may deviate from the set irradiation position $19V_t$ because of, for example, a change over time. Therefore, the console 12 according to this embodiment updates the set irradiation position $19V_t$ to the irradiation position $19_r$, which is the actual irradiation position, to estimate the actual irradiation position $19_r$. This will be described in detail below.

The irradiation positions $19_r$, which are the actual positions of the radiation source 29 in a case in which the projection images 80 are captured in the tomosynthesis imaging, may deviate from the set irradiation positions $19V_t$ because of, for example, a change over time. The set irradiation positions $19V_t$ are set as the irradiation positions used in a case in which the second tomographic image generation unit, which will be described in detail below, generates the tomographic images 82 (see FIG. 8). A design irradiation position is given as an example of the set irradiation position $19V_t$. As described above, in some cases, the actual irradiation position $19_t$ in the tomosynthesis imaging is different from the set irradiation position $19V_t$. Therefore, the console 12 according to this embodiment estimates the actual irradiation position $19_r$. This will be described in detail below.

In addition, as illustrated in FIG. 3, the irradiation angle of the radiation R means an angle α formed between a normal line CL to the detection surface 20A of the radiation detector 20 and a radiation axis RC. The radiation axis RC means an axis that connects the focus of the radiation source 29 at each irradiation position 19 and a preset position such as the center of the detection surface 20A. Further, here, it is assumed that the detection surface 20A of the radiation detector 20 is substantially parallel to the imaging surface 24A.

On the other hand, in a case in which the mammography apparatus 10 performs the normal imaging, the radiation source 29 of the radiation emitting unit 28 remains at the irradiation position $19_t$ (the irradiation position $19_t$ along the normal direction, the irradiation position $19_4$ in FIG. 3) where the irradiation angle α is 0 degrees. The radiation source 29 emits the radiation R in response to an instruction from the console 12, and the radiation detector 20 captures a radiographic image.

Figure 4:
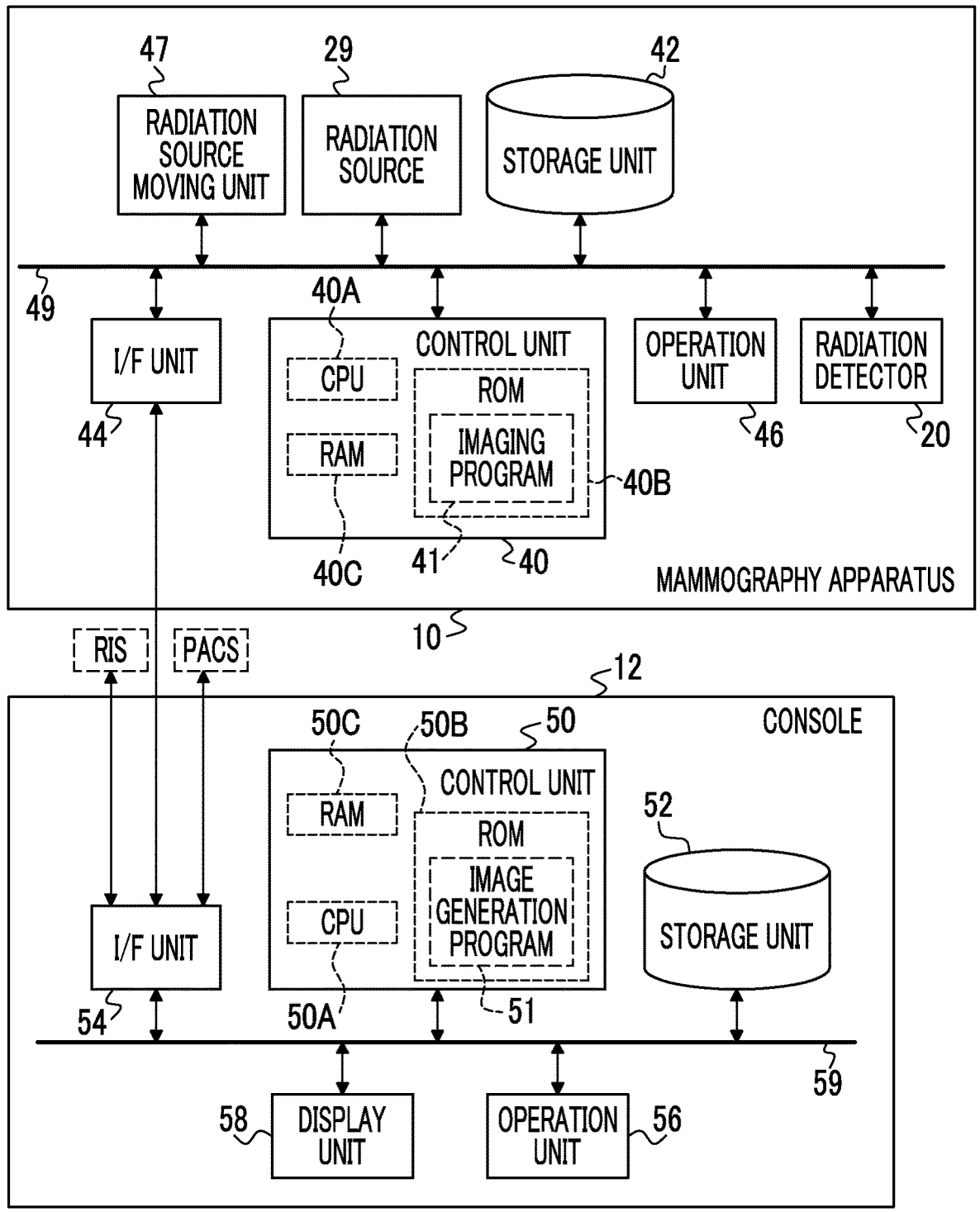
FIG. 4 is a block diagram illustrating an example of the configuration of a mammography apparatus and a console according to the embodiment.

Further, FIG. 4 is a block diagram illustrating an example of the configuration of the mammography apparatus 10 and the console 12 according to the embodiment. As illustrated in FIG. 4, the mammography apparatus 10 according to this embodiment further comprises a control unit 40, a storage unit 42, an interface (I/F) unit 44, an operation unit 46, and a radiation source moving unit 47. The control unit 40, the storage unit 42, the I/F unit 44, the operation unit 46, and the radiation source moving unit 47 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. For example, various programs including an imaging program 41 which is executed by the CPU 40A and which performs control related to the capture of a radiographic image are stored in the ROM 40B in advance. The RAM 40C temporarily stores various kinds of data.

For example, the image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

The radiation source moving unit 47 has a function of moving the radiation source 29 to each of the plurality of irradiation positions 19 under the control of the control unit 40 in a case in which the tomosynthesis imaging is performed as described above. Specifically, the radiation source moving unit 47 rotates the arm portion 33 with respect to the imaging table 24 to move the radiation source 29 to each of the plurality of irradiation positions 19. The radiation source moving unit 47 according to this embodiment is provided inside the arm portion 33.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 4, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C.

Various programs which are executed by the CPU 50A and which include an image generation program 51 are stored in the ROM 50B in advance. The RAM 50C temporarily stores various kinds of data. In this embodiment, the CPU 50A is an example of a processor according to the present disclosure, and the console 12 is an example of an image processing device according to the present disclosure. In addition, the image generation program 51 according to this embodiment is an example of an image processing program according to the present disclosure.

For example, the image data of the radiographic image captured by the mammography apparatus 10 and various other kinds of information are stored in the storage unit 52. A specific example of the storage unit 52 is an HDD, an SSD, or the like.

The operation unit 56 is used by the user to input, for example, instructions which are related to the capture of a radiographic image and which include an instruction to emit the radiation R, or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 5:
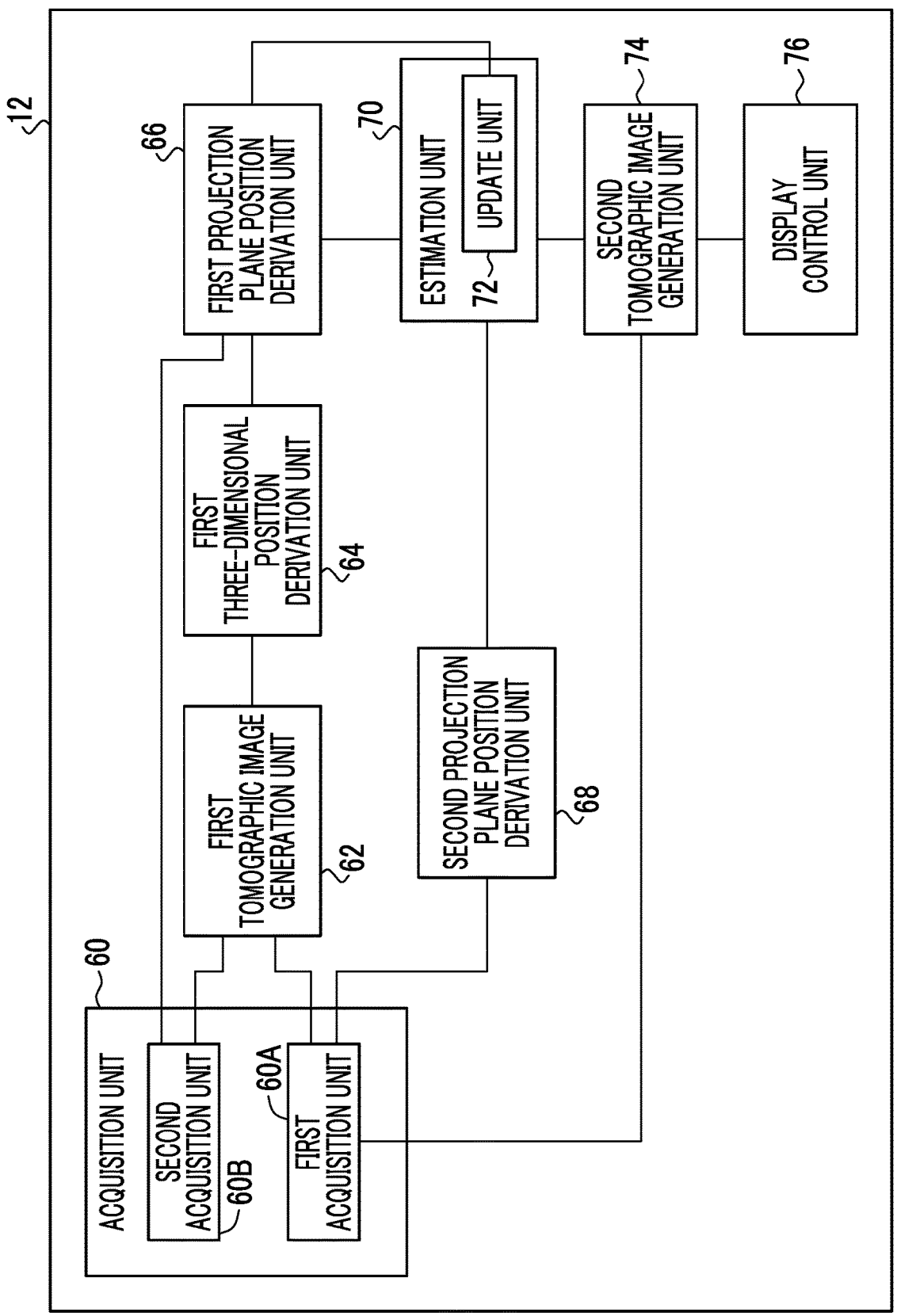
FIG. 5 is a functional block diagram illustrating an example of the functions of the console according to the embodiment.

The console 12 according to this embodiment has a function of estimating the actual irradiation positions $19_t$ in a case in which a plurality of projection images are projected in the tomosynthesis imaging. FIG. 5 is a functional block diagram illustrating an example of a configuration related to a function of estimating the actual irradiation positions $19_t$ in a case in which a plurality of projection images are projected in the tomosynthesis imaging in the console 12 according to this embodiment. As illustrated in FIG. 5, the console 12 comprises an acquisition unit 60, a first tomographic image generation unit 62, a first three-dimensional position derivation unit 64, a first projection plane position derivation unit 66, a second projection plane position derivation unit 68, an estimation unit 70, a second tomographic image generation unit 74, and a display control unit 76. For example, in the console 12 according to this embodiment, the CPU 50A of the control unit 50 executes the image generation program 51 stored in the ROM 50B to function as the acquisition unit 60, the first tomographic image generation unit 62, the first three-dimensional position derivation unit 64, the first projection plane position derivation unit 66, the second projection plane position derivation unit 68, the estimation unit 70, the second tomographic image generation unit 74, and the display control unit 76. The functions of each unit will be described with reference to FIGS. 6 and 7.

Figure 6:
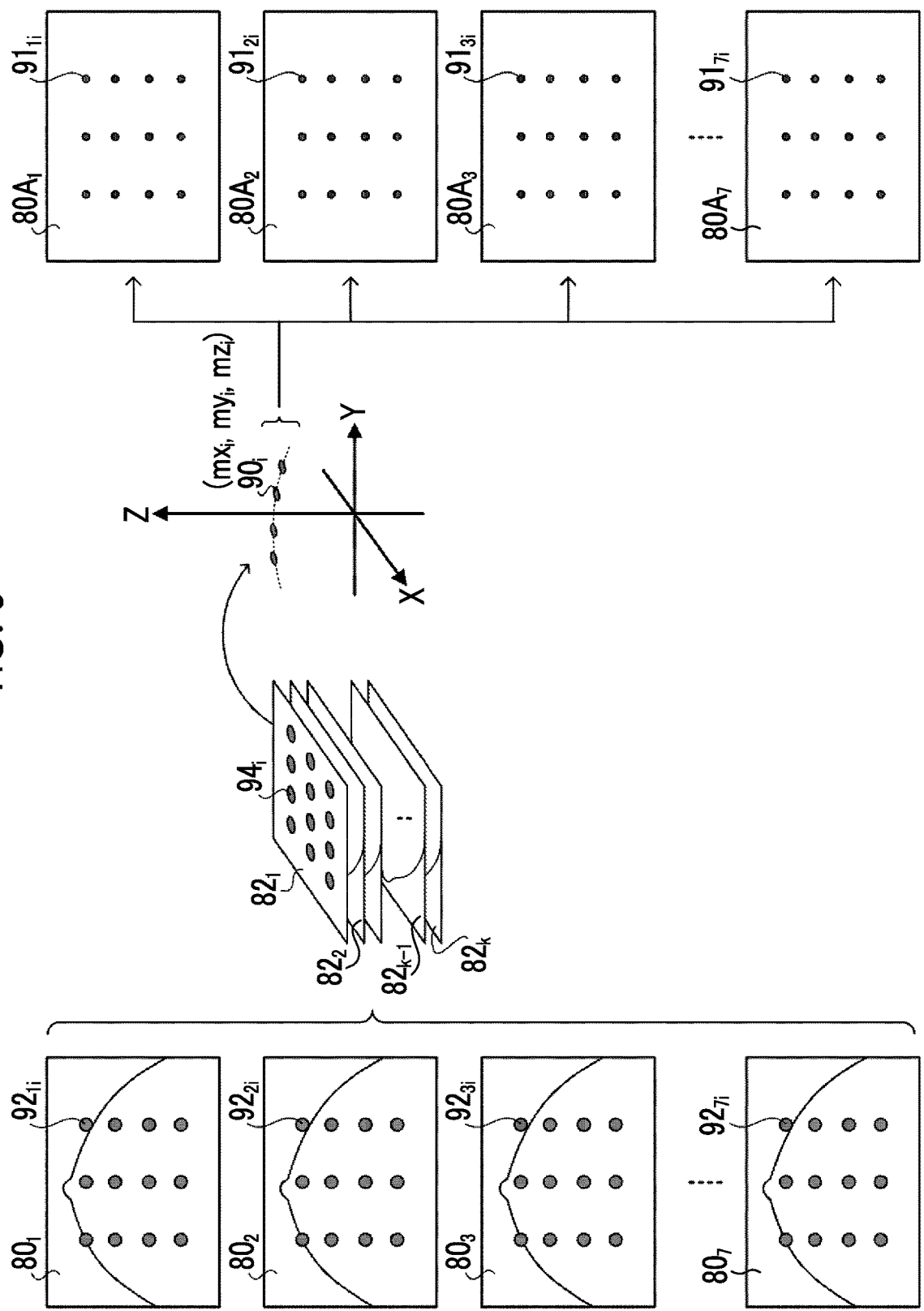
FIG. 6 is a diagram illustrating the functions of the console.

The acquisition unit 60 includes a first acquisition unit 60A and a second acquisition unit 60B. The first acquisition unit 60A has a function of acquiring a plurality of projection images $80_t$ in which the markers $90_i$ are included. The first acquisition unit 60A according to this embodiment acquires image data indicating projection images $80_1$ to $80_7$ (see FIG. 6) obtained by the tomosynthesis imaging in the mammography apparatus 10. Each of the projection images $80_t$ acquired by the first acquisition unit 60A includes marker images $92_{ti}$ indicating the markers $90_i$. In this embodiment, as illustrated in FIG. 6, the projection image $80_1$ includes marker images $92_{1i}$, the projection image $80_2$ includes marker images $92_{2i}$, and the projection image $80_3$ includes marker images $92_{3i}$. Further, the projection image $80_7$ includes marker images $92_{7i}$. The first acquisition unit 60A outputs the acquired image data indicating the projection images $80_1$ to $80_7$ to the first tomographic image generation unit 62, the first projection plane position derivation unit 66, and the second projection plane position derivation unit 68.

The second acquisition unit 60B has a function of acquiring a plurality of set irradiation positions $19V_t$ set as the irradiation positions of the plurality of projection images $80_t$ acquired by the first acquisition unit 60A. The second acquisition unit 60B according to this embodiment acquires the coordinates $(sx_t, sy_t, sz_t)$ of the set irradiation positions $19V_t$ in the three-dimensional space as the set irradiation positions $19V_t$. A method by which the second acquisition unit 60B acquires the set irradiation positions $19V_t$ is not particularly limited. For example, the second acquisition unit 60B may acquire information indicating the set irradiation positions $19V_t$ from the mammography apparatus 10. Further, for example, in a case in which the information indicating the set irradiation positions $19V_t$ is given as imaging information to the projection images, the information indicating the set irradiation positions $19V_t$ may be acquired from the imaging information given to the acquired projection images. The second acquisition unit 60B outputs the acquired coordinates ($sx_t$, $sy_t$, $sz_t$) of the plurality of set irradiation positions $19V_t$ to the first tomographic image generation unit 62 and the first projection plane position derivation unit 66.

The first tomographic image generation unit 62 has a function of generating tomographic images 82 from the plurality of projection images $80_t$ using the plurality of set irradiation positions $19V_t$. As illustrated in FIG. 6, the first tomographic image generation unit 62 according to this embodiment generates k tomographic images $82_1$ to $82_k$ from the projection images $80_1$ to $80_7$ using the set irradiation positions $19V_t$. Hereinafter, in a case in which the tomographic images $82_1$ to $82_k$ are generically referred to without being distinguished from each other, they are referred to as "tomographic images 82". The tomographic image 82 according to this embodiment is an example of a first tomographic image according to the present disclosure. A method by which the first tomographic image generation unit 62 generates the tomographic images 82 is not particularly limited, and a known method may be used. For example, reconstruction may be performed by a back projection method, such as a filter back projection (FBP) method or an iterative reconstruction method, or a known technique may be applied. In addition, the tomographic plane of the tomographic image 82 generated by the first tomographic image generation unit 62 is substantially parallel to the detection surface 20A of the radiation detector 20 and is substantially parallel to the imaging surface 24A of the imaging table 24. The position of the tomographic plane of the tomographic image 82 generated by the first tomographic image generation unit 62, that is, the height of the tomographic plane from the imaging surface 24A of the imaging table 24, is not particularly limited. Specifically, the height of the tomographic plane can be determined according to, for example, the size of a region of interest, the quality of the radiographic image, the processing load of arithmetic processing in the generation of the tomographic image, and an instruction from the user.

Marker images $94_i$ indicating the markers $90_i$ are included in a tomographic image 82 corresponding to the height at which the markers $90_i$ are present, that is, the position in the Z-axis direction, among the tomographic images $82_1$ to $82_k$. As illustrated in FIG. 2, the markers $90_i$ are provided on the upper surface 38AA of the compression portion 38A of the compression plate 38. Therefore, the marker images $94_i$ are included in the tomographic image 82 corresponding to the height of the upper surface 38AA. In the example illustrated in FIG. 6, the marker images $94_i$ are included in the tomographic image $82_1$ at the highest position, that is, the position close to the radiation source 29. In addition, the tomographic image $82_1$ does not include an image indicating the breast which is the object U. On the other hand, since the tomographic images $82_2$ to $82_k$ correspond to portions below the compression plate 38, they do not include the marker images $94_i$ and include the image indicating the breast which is the object U.

The first tomographic image generation unit 62 outputs image data indicating the generated k tomographic images 82 to the first three-dimensional position derivation unit 64.

The first three-dimensional position derivation unit 64 derives three-dimensional positions where the markers $90_i$ are disposed from the tomographic image 82. The first three-dimensional position derivation unit 64 according to this embodiment derives the coordinates ($mx_i$, $my_i$, $mz_i$) of the markers $90_i$ in the three-dimensional space as the positions of the markers $90_i$. A method by which the first three-dimensional position derivation unit 64 derives the coordinates ($mx_i$, $my_i$, $mz_i$) of the markers $90_i$ from the tomographic image 82 is not particularly limited. For example, in this embodiment, the XY coordinate values of each pixel of the tomographic image 82 are predetermined, and a Z coordinate value is predetermined according to the height of the tomographic image 82. The first three-dimensional position derivation unit 64 extracts the tomographic image $82_1$ including the marker images $94_i$ from the tomographic images $82_1$ to $82_k$ and specifies the center of gravity of each marker image $94_i$ as the position of each marker image $94_i$ included in the tomographic image $82_1$. The first three-dimensional position derivation unit 64 derives the coordinates ($mx_i$, $my_i$, $mz_i$) as the position of each marker $90_i$ from the XY coordinate values of the pixel corresponding to the center of gravity of each marker image $94_i$ and the Z coordinate value associated with the tomographic image $82_1$.

A method by which the first three-dimensional position derivation unit 64 detects the position of each marker image $94_i$ included in the tomographic image $82_1$ is not particularly limited. For example, a method of detecting the marker images $94_i$ using template matching may be applied. Further, for example, a method may be applied which uses a trained model consisting of a neural network that has been subjected to deep learning to detect the marker images $94_i$ using the known marker images $94_i$ as training data. The trained model may consist of, for example, a support vector machine (SVM), a convolutional neural network (CNN), and a recurrent neural network (RNN) in addition to the neural network subjected to deep learning.

Further, in the tomographic image $82_1$, a region including the marker images $94_i$ corresponding to each marker $90_i$ is predetermined. Therefore, the first three-dimensional position derivation unit 64 may detect the position of each marker image $94_i$ included in the tomographic image $82_1$ in the region that is predetermined to include the marker images $94_i$. In this case, it is possible to reduce the processing load required for detecting the marker images $94_i$ and to shorten the processing time.

In addition, in some cases, the set irradiation positions $19V_t$ used to generate the tomographic images 82 are different from the actual irradiation positions $19_t$ in the tomosynthesis imaging as described above. In a case in which the set irradiation positions $19V_t$ are different from the irradiation positions $19_t$ as described above, the coordinates ($mx_i$, $my_i$, $mz_i$) of the position of each marker $90_i$ derived by the first three-dimensional position derivation unit 64 are different from the actual position of the marker $90_i$.

The first three-dimensional position derivation unit 64 outputs the derived coordinates ($mx_i$, $my_i$, $mz_i$) of the position of each marker $90_i$ to the first projection plane position derivation unit 66.

The first projection plane position derivation unit 66 has a function of deriving the projection plane positions of the markers $90_i$ projected onto the projection plane 80A from the set irradiation positions $19V_t$ and the positions of the markers $90_i$. In a case in which the radiation source 29 emits the radiation R at the set irradiation positions $19V_t$ to capture the projection images $80_t$, the projection plane positions of the markers $90_i$ derived by the first projection plane position derivation unit 66 correspond to the positions of the marker images $92_{ti}$ indicating the markers $90_i$ included in the captured projection images $80_t$. In this case, the first projection plane position derivation unit 66 derives the positions of the marker images $92_{ti}$ as the projection plane positions.

Figure 7:
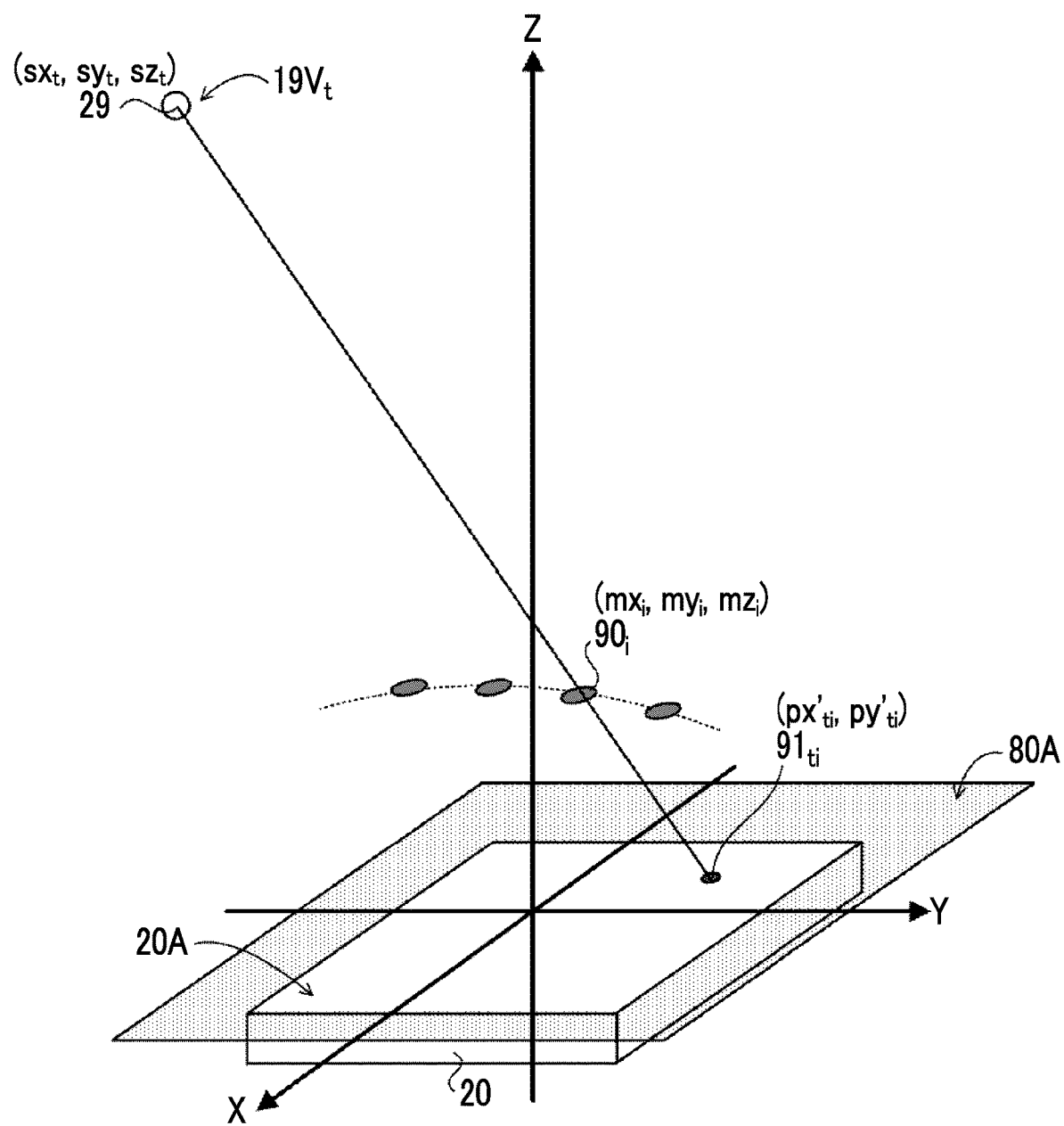
FIG. 7 is a diagram illustrating the derivation of a projection plane position of a marker in a projection plane.

A method for deriving the projection plane positions of the markers $90_i$ in the first projection plane position derivation unit 66 according to this embodiment will be described with reference to FIG. 7. In FIG. 7, the region of the projection plane 80A corresponding to the projection image $80_t$ corresponding to each irradiation position $19_t$ is illustrated as a projection plane $80A_t$, and the positions of the markers $90_i$ in the projection plane $80A_t$ are illustrated as marker images $91_{ti}$.

As illustrated in FIG. 7, it is assumed that the coordinates of the position of each set irradiation position $19V_t$ are $(sx_t, sy_t, sz_t)$, and the coordinates of the marker image $91_{ti}$ indicating the position of the marker $90_i$ in the projection plane 80A are $(px'_{ti}, py'_{ti})$. The value of the coordinate $px'_{ti}$ is represented by the following Expression (1). In addition, the value of the coordinate $py'_{ti}$ is represented by the following Expression (2).

$$px'_{ti} = \frac{mx_i sz_t - sx_t mz_i}{sz_t - mz_i} \quad (1)$$

$$py'_{ti} = \frac{my_i sz_t - sy_t mz_i}{sz_t - mz_i} \quad (2)$$

The first projection plane position derivation unit 66 derives the coordinates $(px'_{ti}, py'_{ti})$ of the marker image $91_{ti}$ as the projection plane position of the marker $90_i$ in the projection plane 80A from the coordinates $(sx_t, sy_t, sz_t)$ of the set irradiation position $19V_t$ and the coordinates $(mx_i, my_i, mz_i)$ of the marker $90_i$ using the above-described Expressions (1) and (2). The coordinates $(px'_{ti}, py'_{ti})$ of the marker images $91_{ti}$ are derived for each irradiation position $19_t$. For example, as illustrated in FIG. 6, the first projection plane position derivation unit 66 derives the coordinates $(px'_{1i}, py'_{1i})$ of the marker images $91_{1i}$ in the projection plane $80A_1$ corresponding to the irradiation position $19_1$, the coordinates $(px'_{2i}, py'_{2i})$ of the marker images $91_{2i}$ in the projection plane $80A_2$ corresponding to the irradiation position $19_2$, and the coordinates $(px'_{3i}, py'_{3i})$ of the marker images $91_{3i}$ in the projection plane $80A_3$ corresponding to the irradiation position $19_3$. Further, the first projection plane position derivation unit 66 derives the coordinates $(px'_{7i}, py'_{7i})$ of the marker images $91_{7i}$ in the projection plane $80A_7$ corresponding to the irradiation position $19_7$. Hereinafter, the coordinates $(px'_{ti}, py'_{ti})$ are referred to as "first two-dimensional coordinates of the marker $90_i$". The first two-dimensional coordinates $(px'_{ti}, py'_{ti})$ of the marker $90_i$ derived by the first projection plane position derivation unit 66 according to this embodiment are an example of a first projection plane position according to the present disclosure.

The first projection plane position derivation unit 66 outputs the derived first two-dimensional coordinates $(px'_{ti}, py'_{ti})$ of the marker $90_i$ to the estimation unit 70.

The second projection plane position derivation unit 68 has a function of deriving the position of the marker $90_i$ in the projection plane 80A from the marker image $92_{ti}$ indicating the marker $90_i$ included in each of the projection images $80_t$. The second projection plane position derivation unit 68 according to this embodiment derives the coordinates $(px_{ti}, py_{ti})$ of the position of the marker image $92_{ti}$ included in the projection image $80_t$ as the position of the marker $90_i$ in the projection plane 80A. Hereinafter, the coordinates $(px_{ti}, py_{ti})$ are referred to as "second two-dimensional coordinates of the marker $90_i$". The second two-dimensional coordinates $(px_{ti}, py_{ti})$ of the marker $90_i$ derived by the second projection plane position derivation unit 68 according to this embodiment are an example of a second projection plane position according to the present disclosure.

A method by which the second projection plane position derivation unit 68 derives the second two-dimensional coordinates $(px_{ti}, py_{ti})$ of the marker $90_i$ from the marker image $92_{ti}$ included in the projection image $80_t$ is not particularly limited. For example, in this embodiment, the XY coordinate values of each pixel of the projection image $80_t$ are predetermined. The second projection plane position derivation unit 68 specifies the center of gravity of each marker image $92_{ti}$ as the position of each marker image $92_{ti}$ included in each projection image $80_t$. The second projection plane position derivation unit 68 derives the second two-dimensional coordinates $(px_{ti}, py_{ti})$ of the marker $90_i$ from the XY coordinate values of the pixel corresponding to the center of gravity of each marker image $92_{ti}$.

The second projection plane position derivation unit 68 outputs the derived second two-dimensional coordinates $(px_{ti}, py_{ti})$ of the marker $90_i$ to the estimation unit 70.

The estimation unit 70 has a function of estimating the irradiation position $19_t$, which is the actual irradiation position in the tomosynthesis imaging, on the basis of the first two-dimensional coordinates $(px'_{ti}, py'_{ti})$ of the marker $90_i$ and the second two-dimensional coordinates $(px_{ti}, py_{ti})$ of the marker $90_i$. As illustrated in FIG. 5, the estimation unit 70 according to this embodiment includes an update unit 72.

The first two-dimensional coordinates $(px'_{ti}, py'_{ti})$ of the marker $90_i$ are a so-called hypothetical two-dimensional position of the marker $90_i$ derived from the three-dimensional position of the marker $90_i$ derived from the tomographic image 82 and the set irradiation position $19V_t$. On the other hand, the second two-dimensional coordinates $(px_{ti}, py_{ti})$ of the marker $90_i$ are a so-called practical two-dimensional position of the marker $90_i$ derived from each projection image $80_t$. The estimation unit 70 brings the first two-dimensional coordinates $(px'_{ti}, py'_{ti})$ of the marker $90_i$, which are the hypothetical two-dimensional position, close to the second two-dimensional coordinates $(px_{ti}, py_{ti})$ of the marker $90_i$, which are the actual two-dimensional position, to estimate the irradiation position $19_t$, which is the actual irradiation position in the tomosynthesis imaging.

As the coordinates $(sx_t, sy_t, sz_t)$ of the set irradiation position $19V_t$ become closer to the actual irradiation position $19_t$, a difference (hereinafter, referred to as a "difference in the two-dimensional position of the marker $90_i$") between the first two-dimensional coordinates $(px'_{ti}, py'_{ti})$ of the marker $90_i$, which are the hypothetical two-dimensional position, and the second two-dimensional coordinates $(px_{ti}, py_{ti})$ of the marker $90_i$, which are the actual two-dimensional position, becomes smaller. Further, as the coordinates $(mx_i, my_i, mz_i)$ of the position of the marker $90_i$ become closer to the position where the marker $90_i$ is actually present, the difference in the two-dimensional position of the marker $90_i$ becomes smaller.

For example, in this embodiment, a square error between the second two-dimensional coordinates $(px_{ti}, py_{ti})$ and the first two-dimensional coordinates $(px'_{ti}, py'_{ti})$ is defined as an energy function E represented by the following Expression (3):

$$E = \sum_t \sum_i \left( (px_{ti} - px'_{ti})^2 + (py_{ti} - py'_{ti})^2 \right) \quad (3)$$

The energy function E represented by Expression (3) becomes smaller as the coordinates $(sx_t, sy_t, sz_t)$ of the set irradiation position $19V_t$ become closer to the actual irradiation position $19_t$. In addition, the energy function E becomes smaller as the coordinates $(mx_i, my_i, mz_i)$ of the position of the marker $90_i$ become closer to the position where the marker $90_i$ is actually present.

In this embodiment, it is assumed that the coordinates $(sx_t, sy_t, sz_t)$ of the set irradiation position $19V_t$ and the coordinates $(mx_i, my_i, mz_i)$ of the marker $90_i$ are used as parameters. The estimation unit 70 derives the coordinates $(sx_t, sy_t, sz_t)$ of the set irradiation position $19V_t$ and the coordinates $(mx_i, my_i, mz_i)$ of the position of the marker $90_i$ at which the energy function E represented by the above-described Expression (3) is minimized, on the basis of the above-described Expressions (1) and (2). As the difference between the second two-dimensional coordinates $(px_{ti}, py_{ti})$ and the first two-dimensional coordinates $(px'_{ti}, py'_{ti})$ becomes smaller, the energy function E becomes smaller. In a case in which the second two-dimensional coordinates $(px_{ti}, py_{ti})$ are equal to the first two-dimensional coordinates $(px'_{ti}, py'_{ti})$, the energy function E is "0". The coordinates $(sx_t, sy_t, sz_t)$ of the set irradiation position $19V_t$ at which the energy function E is minimized correspond to the actual irradiation position $19_t$ in the tomosynthesis imaging, and the coordinates $(mx_i, my_i, mz_i)$ of the position of the marker $90_i$ correspond to the actual three-dimensional position of the marker $90_i$.

Therefore, the estimation unit 70 repeatedly updates each of the coordinates $(sx_t, sy_t, sz_t)$ of the set irradiation position $19V_t$ and the coordinates $(mx_i, my_i, mz_i)$ of the marker $90_i$ which are the parameters of the energy function E using the update unit 72 to derive the energy function E represented by the above-described Expression (3).

The update unit 72 has a function of updating each of the coordinates $(sx_t, sy_t, sz_t)$ of the set irradiation position $19V_t$ and the coordinates $(mx_i, my_i, mz_i)$ of the marker $90_i$. For example, the update unit 72 according to this embodiment updates the coordinates $(mx_i, my_i, mz_i)$ of the marker $90_i$ within the range of the disposition condition of the markers $90_i$. As described above, the markers $90_i$ are disposed on the upper surface 38AA of the compression portion 38A of the compression plate 38 under the disposition condition in which the markers $90_i$ are disposed at the interval L1 in the X direction and at the interval L2 in the Y direction. That is, the disposition condition of the markers $90_i$ is that adjacent markers $90_i$ are disposed at the intervals L1 and L2. Therefore, the positions of the markers $90_i$ are limited by the intervals L1 and L2. In this embodiment, the update unit 72 updates the coordinates $(mx_i, my_i, mz_i)$ of the marker $90_i$ within the range of the disposition condition to suppress the amount of processing for minimizing the energy function E. In addition, the disposition condition of the markers $90_i$ is not limited to this aspect. An example of the disposition condition of the markers $90_i$ is a condition corresponding to a bending state of the compression portion 38A of the compression plate 38, an inclination state of the compression plate 38 attached to the compression unit 36, and a rotation state of the compression plate 38 attached to the compression unit 36.

Further, for example, the update unit 72 according to this embodiment updates the coordinates $(sx_t, sy_t, sz_t)$ of the set irradiation positions $19V_t$ within the range of the disposition condition of the set irradiation positions $19V_t$. In this embodiment, the interval between the set irradiation positions $19V_t$ is predetermined as the disposition condition. Therefore, the positions of the set irradiation positions $19V_t$ are limited by the disposition condition. In this embodiment, the update unit 72 updates the coordinates $(sx_t, sy_t, sz_t)$ of the set irradiation positions $19V_t$ within the range of the disposition condition to suppress the amount of processing for minimizing the energy function E.

The estimation unit 70 minimizes the energy function E represented by the above-described Expression (3) in this way to estimate the coordinates of the actual irradiation positions $19_t$ and the coordinates of the actual three-dimensional positions of the markers $90_i$ in the tomosynthesis imaging. The estimation unit 70 outputs the coordinates of the actual irradiation positions $19_t$ and the coordinates of the actual three-dimensional positions of the markers $90_i$ in the tomosynthesis imaging to the second tomographic image generation unit 74.

The second tomographic image generation unit 74 has a function of generating tomographic images from the projection images $80_t$ using the irradiation positions $19_t$ estimated by the estimation unit 70. The tomographic image generated by the second tomographic image generation unit 74 according to this embodiment is an example of a second tomographic image according to the present disclosure. A method by which the second tomographic image generation unit 74 generates the tomographic images is not particularly limited, and a known method can be used. For example, the same method as that by which the first tomographic image generation unit 62 generates the tomographic images 82 can be applied. In addition, the second tomographic image generation unit 74 according to this embodiment generates the tomographic images up to a height corresponding to the actual three-dimensional position of the marker $90_i$ in the height direction estimated by the estimation unit 70. That is, the second tomographic image generation unit 74 sets the highest position of the tomographic plane of the generated tomographic image, in other words, the height of the tomographic plane of the tomographic image closest to the radiation source 29 as the height at which the marker $90_i$ is disposed. As described above, the markers $90_i$ are disposed on the upper surface 38AA of the compression portion 38A of the compression plate 38. Therefore, in a case in which the height (the position in the Z-axis direction) of the marker $90_i$ is known, the thickness of the breast compressed by the compression plate 38 is known. For this reason, the second tomographic image generation unit 74 derives the thickness of the breast on the basis of the height of the marker $90_i$ and generates tomographic images up to the height corresponding to the derived thickness of the breast. Therefore, the tomographic image generated by the second tomographic image generation unit 74 does not include the image indicating the marker $90_i$. As a result, for example, it is possible to suppress the number of tomographic images generated by the second tomographic image generation unit 74, as compared to a case in which the tomographic images are generated up to the height of the marker $90_i$, and thus to suppress the amount of processing required to generate the tomographic images. Further, since the tomographic images do not include the image indicating the marker $90_i$, the image indicating the marker $90_i$ is not included in a composite two-dimensional image in a case in which the composite two-dimensional image is generated from a plurality of generated tomographic images. As described above, the second tomographic image generation unit 74 may further generate a composite two-dimensional image from the generated tomographic images. In addition, a method by which the second tomographic image generation unit 74 generates the composite two-dimensional image is not particularly limited. A known method, such as the method described in U.S. Pat. No. 8,983,156B or the method described in JP2014-128716A, can be used.

However, it is known that, as the thickness of the breast becomes larger, the amount of scattered radiation generated becomes larger. Therefore, the second tomographic image generation unit 74 according to this embodiment estimates the amount of scattered radiation on the basis of the thickness of the breast derived as described above. Further, the second tomographic image generation unit 74 applies a constant frequency removal filter that removes low-frequency components corresponding to the estimated amount of scattered radiation to the projection images $80_t$ to remove scattered radiation components from the projection images $80_t$. The second tomographic image generation unit 74 generates tomographic images from the projection images $80_t$ from which the scattered radiation has been removed. In addition, a correspondence relationship between the thickness of the breast and the low-frequency component removal filter applied to remove the scattered radiation is obtained, which makes it possible to select a low-frequency component removal filter to be applied to remove the scattered radiation from the derived thickness of the breast even in a case in which the second tomographic image generation unit 74 does not estimate the amount of scattered radiation corresponding to the thickness of the breast.

Further, the second tomographic image generation unit 74 according to this embodiment derives information related to the amount of mammary glands in the breast which is the object U on the basis of the tomographic images generated from the projection images $80_t$. For example, the second tomographic image generation unit 74 according to this embodiment derives a mammary gland content indicating the content of the mammary glands in the thickness direction of the breast, which is the irradiation direction of the radiation R, as the information related to the amount of mammary glands for each pixel. In a case in which there are no mammary glands and the breast consists of only fat, the mammary gland content is "0". As the value of mammary gland density becomes larger, the mammary gland content becomes larger. In addition, a method by which the second tomographic image generation unit 74 derives the mammary gland content is not particularly limited, and a known method can be applied. For example, the second tomographic image generation unit 74 can derive the mammary gland content on the basis of pixel values of a region that does not include the object in each tomographic image, that is, a so-called blank region, pixel values of pixels corresponding to fat, pixel values of the pixels for which the mammary gland content is derived, and an average attenuation coefficient ratio between the mammary gland and fat (an average attenuation coefficient of the mammary gland/an average attenuation coefficient of fat).

In a case in which the mammary gland density of the breast is high, that is, in a case of a so-called dense breast, there is a concern that the mammary glands will hide a region of interest, such as tumor mass. For this reason, it is desirable that the amount of mammary glands or mammary gland density of the breast is derived to derive the mammary gland content with higher accuracy. As described above, the thickness of the breast is involved in the derivation of the mammary gland density. However, in a case in which the breast is compressed by the compression plate 38, the thickness of the breast may not be uniform because of the bending or inclination of the compression plate 38. Therefore, in this embodiment, a plurality of markers $90_i$ are provided on the upper surface 38AA of the compression portion 38A of the compression plate 38, which makes it possible for the second tomographic image generation unit 74 to derive the thickness of the breast in a local region. Therefore, the second tomographic image generation unit 74 according to this embodiment can derive the amount of mammary glands with higher accuracy.

The second tomographic image generation unit 74 may derive a breast category corresponding to the mammary gland content of, for example, the above-described dense breast, using the position of each marker image $94_i$ included in the tomographic image $82_1$ as the information related to the amount of mammary glands. The breast categories include, for example, "fatty", "scattered fibroglandular", "heterogeneously dense", and "(extremely) dense" categories as described in the mammography guidelines.

In addition, the second tomographic image generation unit 74 may derive other information from the thickness of the breast. For example, there is a correspondence relationship between the thickness of the breast and the hardening of the radiation R. As the thickness of the breast becomes larger, the degree of hardening of the radiation becomes larger. Therefore, the second tomographic image generation unit 74 may derive the degree of hardening of the radiation from the thickness of the breast.

The second tomographic image generation unit 74 outputs image data indicating the generated tomographic images to the display control unit 76. In addition, the second tomographic image generation unit 74 outputs the information related to the derived amount of mammary glands to the display control unit 76.

The display control unit 76 has a function of displaying the tomographic images generated by the second tomographic image generation unit 74 on the display unit 58. In addition, the second tomographic image generation unit 74 has a function of displaying the information related to the amount of mammary glands derived by the second tomographic image generation unit 74 on the display unit 58. Further, the display destination of the tomographic images and the information related to the amount of the mammary glands is not limited to the display unit 58. For example, the display destination may be an image reading device or the like outside the radiography system 1. In addition, the display destinations of the tomographic images and the information related to the amount of mammary glands may be different from each other.

Next, the operation of the console 12 in the tomosynthesis imaging will be described with reference to the drawings. After the mammography apparatus 10 performs the tomosynthesis imaging, the console 12 generates a tomographic image using a plurality of projection images obtained by the tomosynthesis imaging and displays the tomographic image on, for example, the display unit 58.

For example, in a case in which the tomosynthesis imaging ends, the mammography apparatus 10 according to this embodiment outputs image data of a plurality of captured projection images $80_t$ to the console 12. The console 12 stores the image data of the plurality of projection images $80_t$ input from the mammography apparatus 10 in the storage unit 52.

Figure 8:
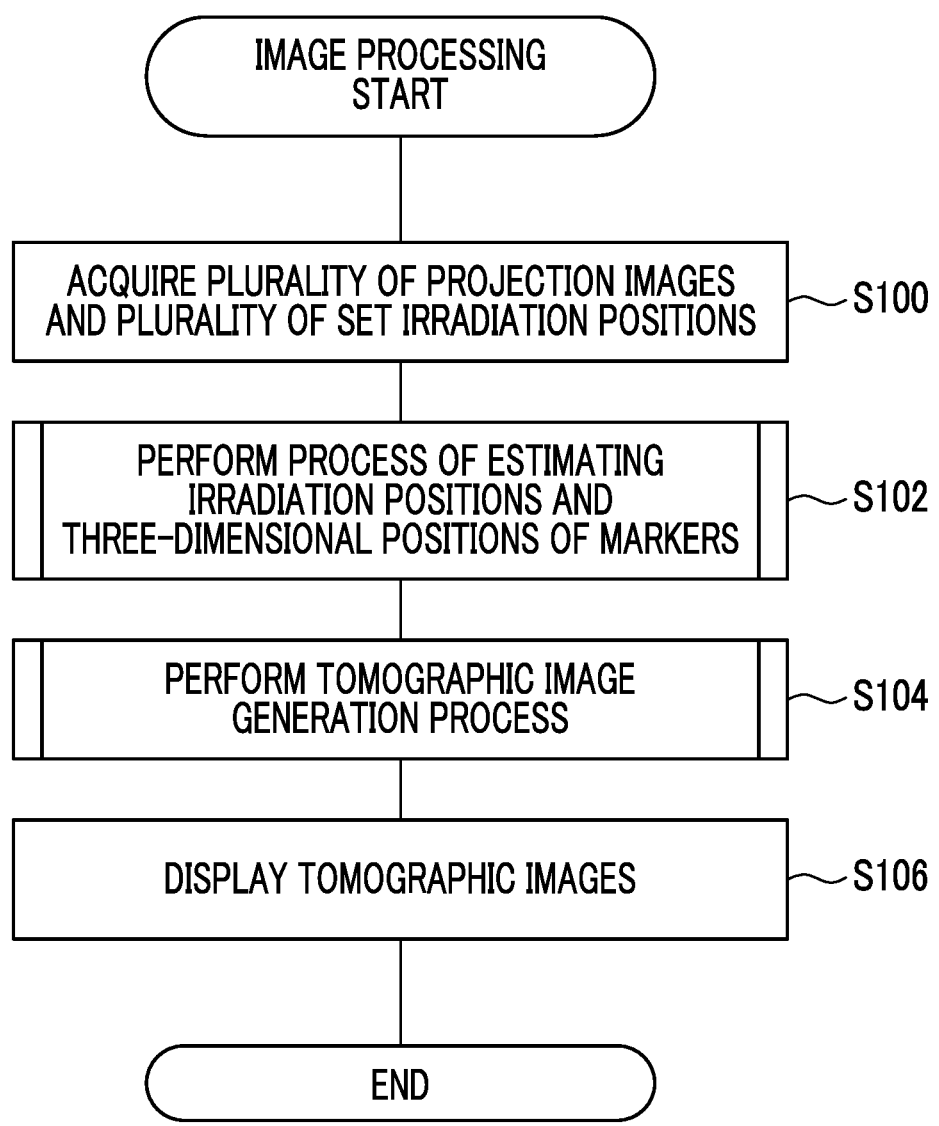
FIG. 8 is a flowchart illustrating an example of the flow of image processing by the console according to the embodiment.

After storing the image data of the plurality of projection images $80_t$ in the storage unit 52, the console 12 performs image processing illustrated in FIG. 8. FIG. 8 is a flowchart illustrating an example of the flow of the image processing performed by the console 12 according to this embodiment. In the console 12 according to this embodiment, for example, the CPU 50A of the control unit 50 executes the image generation program 51 stored in the ROM 50B to perform the image processing whose example is illustrated in FIG. 8.

In Step S100 of FIG. 8, the acquisition unit 60 acquires a plurality of projection images 80$_t$ and a plurality of set irradiation positions 19V$_t$. As described above, the first acquisition unit 60A of the acquisition unit 60 according to this embodiment acquires the image data of the plurality of projection images 80$_t$ from the storage unit 52. Further, the second acquisition unit 60B of the acquisition unit 60 acquires the set irradiation positions 19V$_t$ associated with the projection images 80$_t$.

Then, in Step S102, the first tomographic image generation unit 62, the first three-dimensional position derivation unit 64, the first projection plane position derivation unit 66, the second projection plane position derivation unit 68, and the estimation unit 70 perform an estimation process (which will be described in detail below) for estimating the actual irradiation positions 19$_t$ and the actual three-dimensional positions of the markers 90$_i$ in the tomosynthesis imaging as described above. As described above, the coordinates of the actual irradiation positions 19$_t$ and the coordinates of the actual three-dimensional positions of the markers 90$_i$ in the tomosynthesis imaging are output to the second tomographic image generation unit 74 by the estimation process.

Then, in Step S104, the second tomographic image generation unit 74 executes a tomographic image generation process, which will be described in detail below, as described above and generates tomographic images from the projection images 80$_t$ using the coordinates of the actual irradiation positions 19$_t$ estimated by the estimation process in Step S102.

Further, in this embodiment, in the tomographic image generation process, the information related to the amount of mammary glands is also derived as described above.

Then, in Step S106, the display control unit 76 displays the tomographic images generated in Step S104 and the information related to the derived amount of mammary glands on the display unit 58. In a case in which the process in Step S106 ends, the image processing illustrated in FIG. 8 ends. In addition, the image or information displayed by the display control unit 76 is not limited to this embodiment. For example, the display control unit 76 may also display the projection images 80$_t$.

Figure 9:
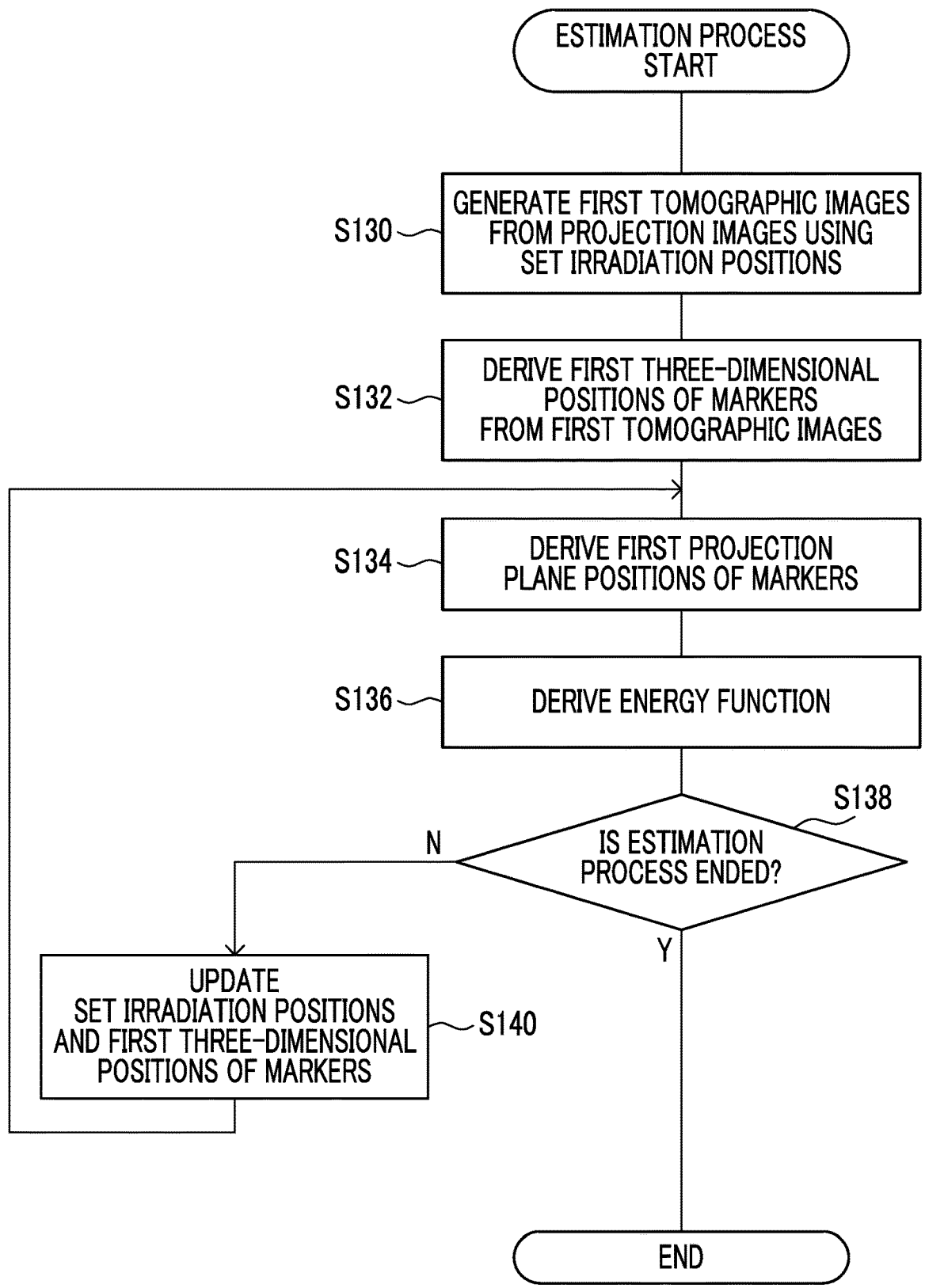
FIG. 9 is a flowchart illustrating an example of the flow of an estimation process in the image processing.

Further, the details of the estimation process in Step S102 of the image processing will be described. FIG. 9 is a flowchart illustrating an example of the flow of the estimation process.

In Step S130 of FIG. 9, the first tomographic image generation unit 62 generates the tomographic images 82 as the first tomographic images from the projection images 80$_t$ using the set irradiation positions 19V$_t$ acquired in Step S100 of the image processing. As described above, the first tomographic image generation unit 62 according to this embodiment generates k tomographic images 82$_1$ to 82$_k$ from the projection images 80$_1$ to 80$_7$ using the set irradiation positions 19V$_t$.

Then, in Step S132, the first three-dimensional position derivation unit 64 derives the three-dimensional positions where the markers 90$_i$ are disposed from the tomographic images 82 generated in Step S130. As described above, the first three-dimensional position derivation unit 64 according to this embodiment derives the coordinates (mx$_i$, my$_i$, mz$_i$) as the position of each marker 90$_i$.

Then, in Step S134, the first projection plane position derivation unit 66 derives the projection plane positions of the markers 90$_i$ projected onto the projection plane 80A from the set irradiation positions 19V$_t$ and the positions of the markers 90$_i$.

Then, in Step S136, the estimation unit 70 derives the energy function E represented by the above-described Expression (3) on the basis of the above-described Expressions (1) and (2).

Then, in Step S138, the estimation unit 70 determines whether or not to end the estimation process. For example, the estimation unit 70 according to this embodiment determines to end the estimation process in a case in which a predetermined end condition is satisfied. An example of the end condition is that the energy function E derived in Step S136 is a minimum value. Further, another example of the end condition is that the energy function E derived in Step S136 is equal to or less than a predetermined threshold value.

In a case in which the end condition is not satisfied, for example, in a case in which the energy function E derived in Step S136 is not the minimum value or in a case in which the energy function E derived in Step S136 is greater than the predetermined threshold value, the determination result in Step S138 is "No", and the process proceeds to Step S140. In Step S140, the update unit 72 of the estimation unit 70 updates the coordinates (sx$_t$, sy$_t$, sz$_t$) of the set irradiation positions 19V$_t$ and the coordinates (mx$_i$, my$_i$, mz$_i$) of the positions of the markers 90$_i$ which are parameters in the derivation of the energy function E. In a case in which the process in Step S140 ends, the process returns to Step S134. Then, the processes in Steps S134 and S136 are repeated.

On the other hand, in a case in which the end condition is satisfied, for example, in a case in which the energy function E derived in Step S136 is the minimum value or in a case in which the energy function E derived in Step S136 is equal to or less than the predetermined threshold value, the determination result in Step S138 is "Yes". The coordinates (sx$_t$, sy$_t$, sz$_t$) of the set irradiation positions 19V$_t$ and the coordinates (mx$_i$, my$_i$, mz$_i$) of the positions of the markers 90$_i$ which are the update results in this case correspond to the estimation results of the estimation process. In a case in which the determination result in Step S138 is "Yes", the estimation process illustrated in FIG. 9 ends, and the process proceeds to Step S104 of the image processing. In addition, the set irradiation positions 19V$_t$ used to generate the tomographic images 82 in the first tomographic image generation unit 62 are updated to the set irradiation positions 19V$_t$ corresponding to these estimation results. Therefore, in a case in which this estimation process is performed in the next tomosynthesis imaging, it is possible to reduce the difference between the set irradiation positions 19V$_t$ and the actual irradiation positions 19$_t$ in the tomosynthesis imaging and thus to reduce the processing load of this estimation process.

Figure 10:
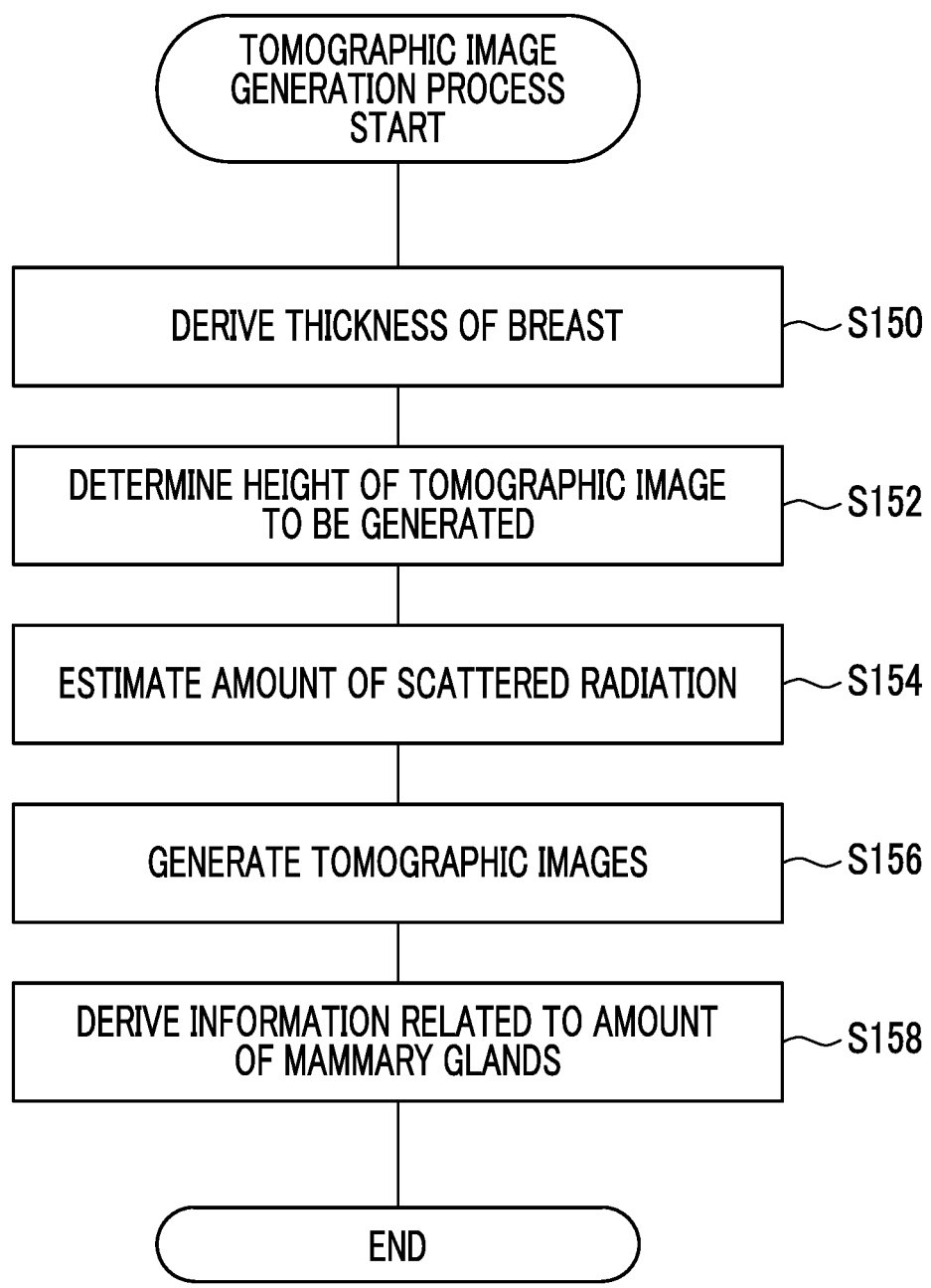
FIG. 10 is a flowchart illustrating an example of the flow of a tomographic image generation process in the image processing.

Further, the details of the tomographic image generation process in Step S104 of the image processing will be described. FIG. 10 is a flowchart illustrating an example of the flow of the tomographic image generation process.

In Step S150 of FIG. 10, the second tomographic image generation unit 74 derives the thickness of the breast compressed by the compression plate 38 on the basis of the height (the position in the Z-axis direction) of the marker 90$_i$ estimated in Step S102 of the image processing.

Then, in Step S152, the second tomographic image generation unit 74 determines the highest position of the tomographic plane of the tomographic image to be generated as described above on the basis of the thickness of the breast derived in Step S150. As described above, the second tomographic image generation unit 74 according to this embodiment determines the height corresponding to the thickness of the breast derived in Step S150 as the height of the tomographic image to be generated.

Then, in Step S154, the second tomographic image generation unit 74 estimates the amount of scattered radiation. As described above, the second tomographic image generation unit 74 estimates the amount of scattered radiation included in each projection image $80_t$ on the basis of the thickness of the breast derived in Step S150.

Then, in Step S156, the second tomographic image generation unit 74 generates tomographic images from the projection images $80_t$ using the coordinates of the actual irradiation positions $19_t$ in the tomosynthesis imaging estimated in Step S102 of the image processing. As described above, the second tomographic image generation unit 74 applies the low-frequency component removal filter corresponding to the amount of scattered radiation estimated in Step S154 to generate tomographic images from the projection images $80_t$.

Then, in Step S158, the second tomographic image generation unit 74 derives information related to the amount of mammary glands in the breast, which is the object U, as described above on the basis of the thickness of the breast derived in Step S150. In a case in which the process in Step S158 ends, the tomographic image generation process illustrated in FIG. 10 ends, and the process proceeds to Step S106 of the image processing.

As described above, the console 12 according to the above-described embodiment processes a plurality of projection images obtained by irradiating the object U with the radiation R emitted from the radiation source 29 at each of the plurality of irradiation positions $19_t$ having different irradiation angles α. The console 12 comprises the CPU 50A. The CPU 50A acquires a plurality of projection images $80_t$ captured at each of a plurality of irradiation positions $19_t$ in a state in which the markers $90_i$ are disposed between the plurality of irradiation positions $19_t$ and the projection plane 80A and a plurality of set irradiation positions $19V_t$ set as the irradiation positions of each of the plurality of projection images $80_t$, generates the tomographic image 82 from the projection images $80_t$ using the set irradiation positions $19V_t$, derives the coordinates ($mx_i$, $my_i$, $mz_i$) of the three-dimensional positions where the markers $90_i$ are disposed from the tomographic images 82, derives the first two-dimensional coordinates ($px'_{ti}$, $py'_{ti}$) of the markers $90_i$ projected onto the projection plane 80A from the set irradiation positions $19V_t$ and the coordinates ($mx_i$, $my_i$, $mz_i$) of the three-dimensional positions of the markers $90_i$, and estimates the irradiation positions $19_t$ on the basis of the second two-dimensional coordinates ($px_{ti}$, $py_{ti}$) of the markers $90_i$ in the projection plane 80A derived from the marker images $92_{ti}$ indicating the markers $90_i$ included in each of the projection images $80_t$ and the first two-dimensional coordinates ($px'_{ti}$, $py'_{ti}$).

The above-described configuration makes it possible for the console 12 according to the above-described embodiment to derive the irradiation position of the radiation R with high accuracy. In addition, the console 12 according to the above-described embodiment can derive the three-dimensional positions of the markers $90_i$ with high accuracy.

Further, in a case in which the three-dimensional positions of the markers $90_i$ are inaccurate, the two-dimensional positions of the markers $90_i$ and the like may also be inaccurate, and the accuracy of deriving the irradiation position of the radiation R may be reduced. In particular, in a case in which the irradiation position of the radiation R is derived using the markers $30_i$ as a reference and the three-dimensional positions of the markers $90_i$ are inaccurate, the accuracy of deriving the irradiation position of the radiation R is reduced. In contrast, the console 12 according to the above-described embodiment can accurately derive both the irradiation position of the radiation R and the three-dimensional positions of the markers $90_i$.

In the tomosynthesis imaging, since a plurality of projection images are captured, a positional deviation between the projection images $80_t$ may occur because of the influence of, for example, the movement of the object. In a case in which the tomographic image 82 is generated using the projection images $80_t$ having a positional deviation therebetween, the quality of the tomographic image 82 deteriorates. Therefore, in some cases, the movement of the object is corrected. The console 12 according to this embodiment corrects the movement of the object using the estimated irradiation positions $19_t$ of the radiation R, which makes it possible to improve the accuracy of correcting the movement.

Furthermore, in the above-described embodiment, the aspect in which the console 12 is an example of the image processing device according to the present disclosure has been described. However, devices other than the console 12 may have the functions of the image processing device according to the present disclosure. In other words, for example, the mammography apparatus 10 or an external device other than the console 12 may have some or all of the functions of the acquisition unit 60, the first tomographic image generation unit 62, the first three-dimensional position derivation unit 64, the first projection plane position derivation unit 66, the second projection plane position derivation unit 68, the estimation unit 70, the second tomographic image generation unit 74 and the display control unit 76. Moreover, the image processing device according to the present disclosure may be configured by a plurality of devices. For example, a device other than the console 12 may have some of the functions of the image processing device.

In addition, in the above-described embodiment, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

Further, in the above-described embodiment, for example, the following various processors can be used as the hardware structure of processing units performing various processes such as the acquisition unit 60, the first tomographic image generation unit 62, the first three-dimensional position derivation unit 64, the first projection plane position derivation unit 66, the second projection plane position derivation unit 68, the estimation unit 70, the second tomographic image generation unit 74 and the display control unit 76. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC).

In this way, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging program 41 is stored (installed) in the ROM 40B in advance and the image generation program 51 is stored (installed) in the ROM 50B in advance has been described. However, the present disclosure is not limited thereto. Each of the imaging program 41 and the image generation program 51 may be recorded on a recording medium, such as a compact disc read only memory (CD-ROM), a digital versatile disc read only memory (DVD-ROM), or a universal serial bus (USB) memory, and then provided. Furthermore, each of the imaging program 41 and the image generation program 51 may be downloaded from an external device through the network.

What is claimed is:

1. An image processing device that processes a plurality of projection images obtained by irradiating an object with radiation emitted from a radiation source at each of a plurality of irradiation positions having different irradiation angles, the image processing device comprising:
at least one processor,
wherein the processor acquires a plurality of projection images captured at each of the irradiation positions in a state in which a marker is disposed between the plurality of irradiation positions and a projection plane, and a plurality of set irradiation positions set as the irradiation positions of the plurality of projection images, generates a first tomographic image from the plurality of projection images using the plurality of set irradiation positions, derives a first three-dimensional position where the marker is disposed from the first tomographic image, derives a first projection plane position of the marker projected onto the projection plane from the plurality of set irradiation positions and the first three-dimensional position of the marker, and estimates the plurality of irradiation positions on the basis of the first projection plane position and a second projection plane position of the marker in the projection plane which is specified from a marker image indicating the marker included in each of the plurality of projection images.

2. The image processing device according to claim 1, wherein the processor estimates the plurality of irradiation positions where the plurality of first projection plane positions and the second projection plane positions are matched with each other.

3. The image processing device according to claim 1, wherein the processor further estimates a second three-dimensional position of the marker on the basis of the plurality of first projection plane positions and the second projection plane positions.

4. The image processing device according to claim 1, wherein the processor generates a second tomographic image from the plurality of projection images using the estimated plurality of irradiation positions.

5. The image processing device according to claim 3, wherein the processor generates a second tomographic image up to a height corresponding to the second three-dimensional position in a height direction from the plurality of projection images, using the estimated plurality of irradiation positions.

6. The image processing device according to claim 3, wherein the processor acquires the plurality of projection images of a breast which is the object and is compressed by a compression member provided with the marker and estimates a thickness of the breast in a compressed state on the basis of the second three-dimensional position.

7. The image processing device according to claim 6, wherein the processor derives information related to an amount of mammary glands of the breast on the basis of the thickness.

8. The image processing device according to claim 6, wherein the processor estimates an amount of scattered radiation on the basis of the thickness.

9. The image processing device according to claim 1, wherein a plurality of the markers are disposed between the plurality of irradiation positions and the projection plane.

10. The image processing device according to claim 1, wherein the processor estimates the plurality of irradiation positions where the plurality of first projection plane positions and the second projection plane positions are matched with each other by repeatedly updating the plurality of set irradiation positions and the first three-dimensional position to repeatedly derive the first projection plane positions.

11. The image processing device according to claim 10, wherein a plurality of the markers are disposed according to a predetermined disposition condition, and
the processor updates the first three-dimensional position within a range of the disposition condition.

12. A radiography system comprising:
a radiation source that generates radiation;
a radiography apparatus that performs tomosynthesis imaging which irradiates an object with the radiation emitted from the radiation source at each of a plurality of irradiation positions having different irradiation angles to capture projection images of the object at each of the irradiation positions; and
the image processing device according to claim 1.

13. An image processing method that is executed by a computer and that processes a plurality of projection images obtained by irradiating an object with radiation emitted from a radiation source at each of a plurality of irradiation positions having different irradiation angles, the image processing method comprising:

acquiring a plurality of projection images captured at each of the irradiation positions in a state in which a marker is disposed between the plurality of irradiation positions and a projection plane, and a plurality of set irradiation positions set as the irradiation positions of the plurality of projection images;

generating a first tomographic image from the plurality of projection images using the plurality of set irradiation positions;

deriving a first three-dimensional position where the marker is disposed from the first tomographic image;

deriving a first projection plane position of the marker projected onto the projection plane from the plurality of set irradiation positions and the first three-dimensional position of the marker; and estimating the plurality of irradiation positions on the basis of the first projection plane position and a second projection plane position of the marker in the projection plane which is specified from a marker image indicating the marker included in each of the plurality of projection images.

14. A non-transitory computer-readable storage medium storing an image processing program that processes a plurality of projection images obtained by irradiating an object with radiation emitted from a radiation source at each of a plurality of irradiation positions having different irradiation angles, the image processing program causing a computer to perform a process comprising:

acquiring a plurality of projection images captured at each of the irradiation positions in a state in which a marker is disposed between the plurality of irradiation positions and a projection plane, and a plurality of set irradiation positions set as the irradiation positions of the plurality of projection images;

generating a first tomographic image from the plurality of projection images using the plurality of set irradiation positions;

deriving a first three-dimensional position where the marker is disposed from the first tomographic image;

deriving a first projection plane position of the marker projected onto the projection plane from the plurality of set irradiation positions and the first three-dimensional position of the marker; and estimating the plurality of irradiation positions on the basis of the first projection plane position and a second projection plane position of the marker in the projection plane which is specified from a marker image indicating the marker included in each of the plurality of projection images.

* * * * *